US012708377B2

(12) United States Patent
Peukert et al.

(10) Patent No.: US 12,708,377 B2
(45) Date of Patent: Aug. 18, 2026

(54) MEDICAL DRILL DEVICE AND MEDICAL DRILL SYSTEM

(71) Applicant: Aesculap AG, Tuttlingen (DE)

(72) Inventors: Andrea Peukert, Tuttlingen (DE); Robert Bruessler, Tuttlingen (DE); Irene Marx, Trossingen (DE)

(73) Assignee: Aesculap AG, Tuttlingen (DE)

( * ) Notice: Subject to any disclaimer, the term of this patent is extended or adjusted under 35 U.S.C. 154(b) by 55 days.

(21) Appl. No.: 18/816,073

(22) Filed: Aug. 27, 2024

(65) Prior Publication Data

US 2024/0415525 A1 Dec. 19, 2024

Related U.S. Application Data

(63) Continuation of application No. PCT/EP2023/054780, filed on Feb. 27, 2023.

(30) Foreign Application Priority Data

Feb. 28, 2022 (DE) ..................... 10 2022 104 674.5

(51) Int. Cl.
*A61B 17/16* (2006.01)
*A61B 17/17* (2006.01)

(52) U.S. Cl.
CPC ...... *A61B 17/1615* (2013.01); *A61B 17/1637* (2013.01); *A61B 17/17* (2013.01)

(58) Field of Classification Search
CPC .................................. A61B 17/1615–17/1642
See application file for complete search history.

(56) References Cited

U.S. PATENT DOCUMENTS 5,372,583 A * 12/1994 Roberts ................. A61M 25/06 604/506
5,908,423 A * 6/1999 Kashuba ............. A61B 17/175 408/127

(Continued)

FOREIGN PATENT DOCUMENTS

CN 109288553 A 2/2019
CN 113693671 A 11/2021

(Continued)

OTHER PUBLICATIONS

Search Report received in International Application No. PCT/EP2023/054780 dated May 23, 2023, with translation, 4 pages.

(Continued)

*Primary Examiner* — Zade Coley
(74) *Attorney, Agent, or Firm* — Christopher A. Rothe; CM Law

(57) ABSTRACT

A medical drilling apparatus includes a cannulated drill having a longitudinal channel extending coaxially with the longitudinal axis of the drill. The drilling apparatus has, at a proximal end, a drilling apparatus coupling portion for coupling to a handle or a drilling machine in a rotationally fixed manner. The drilling apparatus also has a mandrin with a distal mandrin portion and a proximal mandrin portion. The distal mandrin portion is configured for inserting and closing the longitudinal channel of the drill over the entire or substantially the entire length of the longitudinal channel of the drill in a drilling position. The drill includes, in the region of its proximal end, a drill coupling portion that forms the drilling apparatus coupling portion together with the proximal mandrin portion. The medical drilling apparatus can be part of a medical drilling system.

20 Claims, 10 Drawing Sheets

(56) References Cited

U.S. PATENT DOCUMENTS 6,200,319 B1* 3/2001 Storer ................ A61B 17/1637 606/79
8,888,779 B2 11/2014 Senn et al.
9,381,024 B2* 7/2016 Globerman ........ A61B 17/1671
2004/0092946 A1* 5/2004 Bagga ................ A61B 17/8858 606/93
2006/0064095 A1 3/2006 Senn et al.
2007/0260184 A1* 11/2007 Justis ..................... A61B 17/16 604/164.01
2008/0065080 A1* 3/2008 Assell ................ A61B 17/7074 606/86 A
2008/0154304 A1* 6/2008 Crawford ........... A61B 17/8819 206/572
2008/0200915 A1* 8/2008 Globerman ........ A61B 17/1671 606/80
2009/0024129 A1 1/2009 Gordon et al.
2009/0228012 A1 9/2009 Gangji et al.
2010/0030221 A1 2/2010 Christian et al.
2014/0257239 A1* 9/2014 Arthur ............... A61B 17/8805 604/506
2018/0049727 A1* 2/2018 Papenfuss ............ A61B 10/025
2021/0244424 A1 8/2021 Suchomel et al.
2021/0315611 A1 10/2021 Sweeney et al.
2023/0404599 A1* 12/2023 Sharifi-Mehr ..... A61B 17/1617

FOREIGN PATENT DOCUMENTS

DE 69924066 T2 1/2006
EP 0995402 B1 4/2000
EP 2263584 A2 12/2010
JP 2010533567 A 10/2010

OTHER PUBLICATIONS

Office Action received in Japanese Application No. 2024-550684 dated Feb. 10, 2026, with translation, 15 pages.

* cited by examiner 18
110
10
14
112
114
60
70
76
118
126
126
124
120
128
134
116
132
34
130
22
122
68
52
48
30
12
32
18
12
46
40
16
42
44
20
30
32
26
36
28
38

18
96
72
70
74
88
30
94
34
98
102
104
92
100
84
90
76
80
108
60
86
22
56
64
58
62
68
52
54
50
20
32
48
16
12
40
44
26
28
36
38
78
82
66

72
74
74
96
22
136
138
92
94
98
84
88
140
142
80
90
60
76
86
100
34
30
58
56
62
68
64
52
50
54
16
12
20
48
32
18
40
46
70
24
78
82
66

18
12
16
30
40
32
20
146
26
28
36
38
144

148

156
150
152
146
154
144

MEDICAL DRILL DEVICE AND MEDICAL DRILL SYSTEM

CROSS-REFERENCE TO RELATED APPLICATIONS

This application is a continuation under 35 U.S.C. § 365 of International Application No. PCT/EP2023/054780, filed on Feb. 27, 2023, and claims priority to German Application No. 10 2022 104 674.5, filed on Feb. 28, 2022. The contents of International Application No. PCT/EP2023/054780 and German Application No. 10 2022 104 674.5 are incorporated by reference herein in their entireties.

FIELD

The present disclosure relates to a medical drilling apparatus comprising a cannulated drill having a longitudinal channel extending coaxially with the longitudinal axis of the drill, wherein the drilling apparatus comprises at a proximal end a drilling apparatus coupling portion for coupling to a handle or a drilling machine in a rotationally fixed manner, wherein the drill has a distal and a proximal end.

The present disclosure further relates to a medical drilling system comprising at least one medical drilling apparatus.

BACKGROUND

In spinal surgery, numerous procedures are performed minimally invasive. As part of spinal stabilization systems, in particular pedicle screws are used, which are placed in the cortical layer of a vertebral region of the pedicle channel. It is known to open the cortex with a drill. After removing the drill, a Kirschner wire or drill wire, hereinafter referred to as a K-wire, is placed into the pre-drilled cortex, by way of which the pedicle screw can then be brought up to the vertebra in order to anchor it in the vertebra in the desired manner. A problem with this approach is that after removing the drill, the entry point in the cortex is hit with the K-wire, because there is no guide for the K-wire for this. In addition, the minimally invasive access point is virtually invisible. A medical drilling apparatus of the type described above with a cannulated drill does not help in this either, since during drilling, bone is pressed into the longitudinal channel, so that the K-wire cannot be placed directly through the drill. The cannulated drill must therefore also be removed first, in order to then place the K-wire in a second step after removing the drill.

SUMMARY

It is therefore an object of the present disclosure to improve a medical drilling apparatus and a medical drilling system of the kind described at the outset such that, in particular, the handling thereof is simplified.

This object is achieved, in accordance with the present disclosure, in a medical drilling apparatus of the kind described at the outset in that the drilling apparatus comprises a mandrin with a distal mandrin portion and a proximal mandrin portion, in that the distal mandrin portion is configured for inserting and closing the longitudinal channel of the drill over the entire or substantially the entire length thereof in a drilling position, and in that the drill comprises in the region of its proximal end a drill coupling portion, which together with the proximal mandrin portion forms the drilling apparatus coupling portion.

A medical drilling apparatus further developed as proposed makes it possible, in particular, to open the bone in a minimally invasive procedure, wherein the drill then does not have to be removed to place a K-wire. Instead, it is sufficient here to remove the mandrin from the longitudinal channel. The mandrin, which completely or nearly completely fills the longitudinal channel, in particular in a positive-locking manner, prevents the ingress of bone substance into the longitudinal channel. After removing the mandrin, the longitudinal channel of the drill is then completely free of bone substance, so that the drill itself can be used as a guide for a K-wire in in order to place said K-wire in the bone, for example in a vertebra, in a defined manner, i.e. in a defined position with a defined orientation. In particular, the mandrin thus forms a closure element in the form of a plug for the longitudinal channel in order to prevent bone substance or other tissue from penetrating into the longitudinal channel and clogging it during drilling. As described, the drill therefore does not have to be removed before the placement of the K-wire, as is the case with conventional methods, but instead itself serves as a guide for the K-wire. This makes it easier to find the entry point on the bone when placing the K-wire and thus also to handle the drilling apparatus. In particular, this improves the quality of the surgical procedure. In addition, it also makes it possible to reduce operating time.

It is favorable if the drilling apparatus coupling portion is of rotationally asymmetrical configuration with respect to the longitudinal axis. The drilling apparatus can thus be coupled in a defined manner to a handle or a drilling machine, for example a drill chuck or a coupling thereof. In particular, a rotationally fixed coupling between the handle or the drilling machine and the drilling apparatus can be created in a simple manner.

It is advantageous if the drill coupling portion has at least one drill entraining face, if the proximal mandrin portion has at least one mandrin entraining face, and if the at least one drill entraining face and the at least one mandrin entraining face abut against one another or substantially abut against one another in the drilling position. In particular, if the stated faces extend in parallel to the longitudinal axis, they make it possible to bring the drill and the mandrin into engagement with one another in the region of the drilling apparatus coupling portion in such a way that the mandrin is co-rotated when the drill rotates. In other words, the drill and the mandrin are rotated together in this way. The proximal mandrin portion and the drill coupling portion mutually form drivers in order to transmit torques to the respective other component, namely, in particular, depending on which component torques are introduced to by the handle or the drilling machine.

A good coupling and guidance of mandrin and drill can be achieved, in particular, by the drill coupling portion having two drill entraining faces and by the proximal mandrin portion having two mandrin entraining faces. In particular, the two respective entraining faces can each be configured extending in parallel to one another pair-wise. For example, the two mandrin entraining faces can point away from one another in opposite directions, and the two drill entraining faces can point toward one another. Of course, it is also conceivable to realize such an alignment or orientation of the entraining faces in reverse.

Preferably, the longitudinal channel has an oval cross-section. In particular, the cross-section may be circular. An oval cross-section also has the advantage that the mandrin is forced to co-rotate when the drill is rotated. A circular cross-section is advantageous because it allows a K-wire with a circular cross-section to be guided through the longitudinal channel and rotated therein in a defined manner.

It is favorable if the distal mandrin portion has a cross-section corresponding to the cross-section of the longitudinal channel. In particular, it is thus possible to fill the longitudinal channel with the distal mandrin portion in a positive-locking manner. The ingress of bone substance into the longitudinal channel can thus be prevented in a simple and secure manner.

Advantageously, a tip is formed at the distal end of the distal mandrin portion. With such a tip, the drilling apparatus can be easily placed on a bone. In particular, a slipping of a tip of the drill can be prevented in a simple and secure manner.

In accordance with a further preferred embodiment, provision may be made that a distal end of the distal mandrin portion in the drilling position reaches up to a distal end of the mandrin channel or projects beyond it. In both cases, it can be ensured, in particular, that the longitudinal channel is sufficiently closed on the distal side to prevent the ingress, in particular, of bone tissue when drilling open a bone. If the distal mandrin portion projects beyond the distal end of the longitudinal channel, it can be used, for example, for positioning the drill on the bone. For this purpose, the distal end of the distal mandrin portion is preferably configured in the form of a tip.

The medical drilling apparatus can be formed in a simple manner if the drilling apparatus coupling portion is of mirror-symmetrical configuration relative to a mirror plane containing the longitudinal axis. In particular, a drilling apparatus coupling portion with a non-round cross-section can thus be formed.

Furthermore, the configuration of the medical drilling apparatus can be simplified if the drill coupling portion and the proximal mandrin portion are each of mirror-symmetrical configuration relative to the mirror plane. In other words, the proximal mandrin portion and the drill coupling portion can be converted into themselves through the mirror plane. Such a configuration makes it possible, in particular, to configure a drill coupling portion with a slot for accommodating the proximal mandrin portion. The slot is then preferably also of mirror-symmetrical configuration relative to the mirror plane.

In order to be able to safely transmit torques from the drill coupling portion to the proximal mandrin portion or vice versa, it is advantageous if the at least one mandrin entraining face and the at least one drill entraining face extend in parallel to the mirror plane.

So that the mandrin co-rotates with the drill, it is favorable if the mandrin and the drill are in engagement with one another in a rotationally fixed manner. A rotation of the drill then leads to a forced rotation of the mandrin.

In accordance with a further preferred embodiment, provision may be made that the mandrin can be brought, with the distal mandrin portion, from a separating position, in which the mandrin and the drill are out of engagement, into the drilling position by inserting the distal mandrin portion into the longitudinal channel commencing from its proximal end. This configuration makes it possible, in particular, to couple the mandrin to the drill in a simple manner. This is advantageous, in particular, if a plurality of pedicle screws are to be placed in the manner described at the outset during a surgical procedure. After the K-wire has been placed, the cannulated drill can be removed. The mandrin can then be brought back into engagement with the drill in the described manner in order to close the longitudinal channel of the drill. Thus, for such a procedure, at least theoretically, only one drill with an associated mandrin is required, and thus only one single drilling apparatus.

It is favorable if a depth stop for the mandrin is arranged or formed on the drill for delimiting an insertion depth of the distal mandrin portion into the longitudinal channel. It can be ensured in this way, in particular, that the mandrin fills the longitudinal channel in the desired manner. For this purpose, a user only has to insert the mandrin into the longitudinal channel up to the depth stop. When the mandrin can no longer be moved further in the distal direction relative to the drill, the mandrin has reached the desired position.

The drilling apparatus can be formed in a simple manner if the depth stop comprises a stop face of the drill pointing in the proximal direction, against which the proximal mandrin portion abuts on the distal side in the drilling position.

Preferably, the stop face extends transversely, in particular perpendicularly, to the longitudinal axis. A depth stop can thus be created in a simple manner.

It is advantageous if the stop face adjoins a proximal insertion opening of the longitudinal channel and surrounds it at least partially, in particular completely. Such a configuration makes it possible, in particular, to form the distal mandrin portion exclusively corresponding to the longitudinal channel in order to fill the longitudinal channel in the drilling position. In this case, the proximal mandrin portion can then exclusively form part of the drilling apparatus coupling portion. Furthermore, a deformation, in particular a bending, of the distal mandrin portion relative to the proximal mandrin portion can thus be prevented in a simple manner.

It is advantageous if the drill coupling portion comprises a coupling slot extending in parallel to the longitudinal axis and if the proximal mandrin portion in the drilling position engages into the coupling slot. This configuration enables, in particular, a simple and defined relative positioning of the proximal mandrin portion and the drill coupling portion. In particular, the proximal mandrin portion can thus be guided on both sides by the drill coupling portion.

It is favorable if the coupling slot has two mutually facing slot faces and if the two slot faces form the two drill entraining faces. In particular, the two slot faces may be configured parallel to one another and parallel to the mirror plane described above. The mirror plane in this case may contain the longitudinal axis or extend in parallel thereto.

Furthermore, a rotationally asymmetrical drilling apparatus coupling portion can be formed in a simple manner, in particular, by the drilling apparatus coupling portion having a coupling face, which extends in parallel to the longitudinal axis and transversely, in particular perpendicularly, to the at least one drill entraining face. For example, this coupling face may be formed on an otherwise rotationally symmetrically configured drilling apparatus coupling portion.

It is favorable if the coupling face is of planar or substantially planar configuration and comprises at least two coupling face portions, if at least one of the at least two coupling face portions is formed by a side face of the drill coupling portion, and if at least one further one of the at least two coupling face portions is formed by a side face of the proximal mandrin portion. In this way, it is possible, in particular, when coupling the drilling apparatus coupling portion to a handle for the drilling apparatus or a drilling machine, to transmit torques not only to the drill, but also at the same time to the mandrin. In particular, a twisting of the proximal mandrin portion and the distal mandrin portion relative to one another can thus be prevented.

The coupling face can be formed in a simple manner if the drilling apparatus coupling portion has a rotationally symmetrical basic shape and a lateral flattened portion extending in parallel to the longitudinal axis.

Preferably, the flattened portion comprises the coupling face. Such a configuration makes it possible, in particular, to bring the drilling apparatus into engagement with a handle or a drilling machine in a simple and secure manner, for example in a rotationally-fixed manner.

In accordance with a further preferred embodiment, provision may be made that the drill coupling portion and the proximal mandrin portion are each individually of rotationally asymmetrical configuration with respect to the longitudinal axis. The two stated portions can thus each be configured as a driver for the other portion in a simple manner in order to transmit torques.

It may further be advantageous if at least one coupling element is arranged or formed on the drilling apparatus coupling portion for predetermining an axial position of the drilling apparatus and a handle or a drilling machine relative to one another. The at least one coupling element makes it possible, in particular, to prevent a relative movement in the axial direction between the drilling apparatus and the handle or the drilling machine in a coupling position.

A handle or a drilling machine can be couped to the drilling apparatus in a simple manner if the at least one coupling element is configured pointing in the radial direction. For example, the at least one coupling element may be configured in the form of a depression pointing in the radial direction, for example in the form of an annular groove or in the form of a portion of an annular groove relative to the longitudinal axis.

A coupling of the drilling apparatus and the handle or drilling machine can be further simplified if the at least one coupling element is configured the form of a coupling projection or a coupling receptacle. Such coupling elements can be brought into engagement with corresponding coupling elements on the handle or on the drilling machine in a force-locking and/or positive-locking manner.

It is favorable if the at least one coupling element is formed at least partially surrounding the longitudinal axis. For example, an annular groove can thus be formed, which extends relative to the longitudinal axis over a circumferential angle that is smaller than 360°. In particular when a coupling face is formed on the drilling apparatus coupling portion as described above, the drilling apparatus coupling portion thereby obtaining a non-round cross-section, it is not necessary for the at least one coupling element to extend over a full circumference with respect to the longitudinal axis, but instead only over a portion of the circumference, for example only over an angular range of 180° or 270°.

Preferably, the at least one coupling element is interrupted by the flattened portion. In other words, there is no coupling element in the region of the flattened portion. In other words, this can be achieved, for example, by dimensioning the flattened portion such that in an originally rotationally symmetrical drilling apparatus coupling portion with a circumferential coupling element with respect to the longitudinal axis, namely extending completely around the longitudinal axis, the coupling element is completely removed in the region of the flattened portion.

Moreover, it may be advantageous if at least one handling element is arranged or is formed on the proximal mandrin portion. Such a handling element can be used, in particular, to engage with a finger or a corresponding pulling element to move the mandrin relative to the drill in the proximal or distal direction. In particular, it is conceivable to provide a pulling element corresponding to the at least one handling element on a handle or a drill chuck of a drilling machine, said pulling element being able to be brought into engagement or out of engagement with the at least one handling element in a targeted manner in order to, as described, move the mandrin relative to the drill in the distal or, in particular, in the proximal direction. In particular when the drill is in the bone with the mandrin accommodated in the longitudinal channel, the mandrin can thus be pulled out of the drill in the proximal direction in a simple manner.

Preferably, the handling element is configured in the form of a handling recess or a handling projection. For example, the handling element can be formed by part of the at least one coupling element, which part is formed on the proximal mandrin portion. In particular, this further simplifies the structure of the drilling apparatus.

In order to be able to easily exert forces acting in the proximal or distal direction on the mandrin, it is advantageous if the at least one handling element is configured pointing in the radial direction relative to the longitudinal axis. For example, the at least one handling element may be configured as part of a circumferential groove on the drilling apparatus coupling portion relative to the longitudinal axis.

The handling of the drilling apparatus can be further simplified if in the drilling position it has an end face extending transversely, in particular perpendicularly, to the longitudinal axis. In particular, said end face can indicate whether the mandrin is in engagement with the drill in the desired manner, i.e., in particular if it fills the longitudinal channel of the drill with the distal mandrin portion.

Furthermore, it is favorable if the proximal mandrin portion defines a proximal mandrin end face, if the drill coupling portion defines a proximal drill end face, and if the end face is formed in part by the mandrin end face and in part by the drill end face. In particular, a user can then directly see whether the mandrin and the drill are in engagement in the desired manner. The end face can thus be used as a sort of visual indicator for a user.

In order to be able to form a sufficiently stable drilling apparatus, it is advantageous if the drill is made of a metallic material. In particular, it may be made of stainless steel or of titanium.

Moreover, it is favorable if the mandrin is made of a metallic material or of a plastic material. A mandrin made of plastic can be produced, in particular, in a cost-effective manner. A mandrin made of a metallic material, in particular, can dissipate heat well that is generated during drilling in addition to the drill.

The drilling apparatus is favorably made of at least one sterilizable material. In particular, it may be made of only one sterilizable material. For example, the mandrin and the drill may be made of the same material.

The object stated at the outset is further achieved, in accordance with the present disclosure, in a drilling system of the kind described at the outset in that the medical drilling apparatus is configured in the form of one of the advantageous embodiments of drilling apparatuses described above and in that the drilling system comprises a handle and/or a drilling machine for coupling to the medical drilling apparatus in a rotationally fixed manner.

The drilling apparatus can be handled with the handle or the drilling machine in the desired manner, in particular in order to drill open a bone, for example for placing a K-wire as a guide for a pedicle screw. The drilling system may also comprise a plurality of drilling apparatuses that differ from one another in shape and size. For example, different kinds of drills may be comprised by the drilling system, for example twist drills, crown drills, core drills, center drills, or countersinking drills.

The drilling system favorably comprises at least one K-wire. Such a K-wire in the sense of this application is a drilling wire. These terms are therefore used synonymously. In particular, it may comprise a plurality of K-wires, for example with different diameters and lengths. After removing the mandrin, the K-wire can, as described, be placed through the longitudinal channel into the bone opened with the drilling apparatus. To this end, it must be long enough to allow the drill to be pulled out. After removing the drill by pulling it in the proximal direction over the K-wire, a cannulated pedicle screw can then be slid over the K-wire in the distal direction and brought up to the bone and screwed into said bone. Preferably, the K-wire is longer than the drill in order to ensure a guided removal.

The handle or the drilling machine can be coupled to the drilling apparatus in a simple manner if the handle and/or the drilling machine comprise a coupling device for coupling to the drilling apparatus coupling portion in a force-locking and/or positive-locking manner in a coupling position.

Preferably, the coupling device can be brought from the coupling position into a release position in which it is out of engagement with the drilling apparatus coupling portion. In the release position, the drilling apparatus can then be removed from the handle or the drilling machine in a simple and secure manner.

It may further be advantageous if the coupling device comprises a pulling element for being brought into engagement with the at least one handling element when the coupling device adopts the release position. As mentioned above, the mandrin can thus be removed from the drill in a simple and secure manner. For this purpose, only the coupling device must be transferred into the release position and the pulling element must be brought into engagement with the at least one handling element. When the handle or the drill is removed from the drilling apparatus in the described position, they still remain coupled to the mandrin but are out of engagement with the drill, such that they pull the mandrin out of the longitudinal channel of the drill when pulled back in the proximal direction.

BRIEF DESCRIPTION OF THE DRAWINGS

The subsequent description of a preferred embodiment of the present disclosure serves in conjunction with the drawings for further explanation. In the drawings.

DETAILED DESCRIPTION

Figure 1:
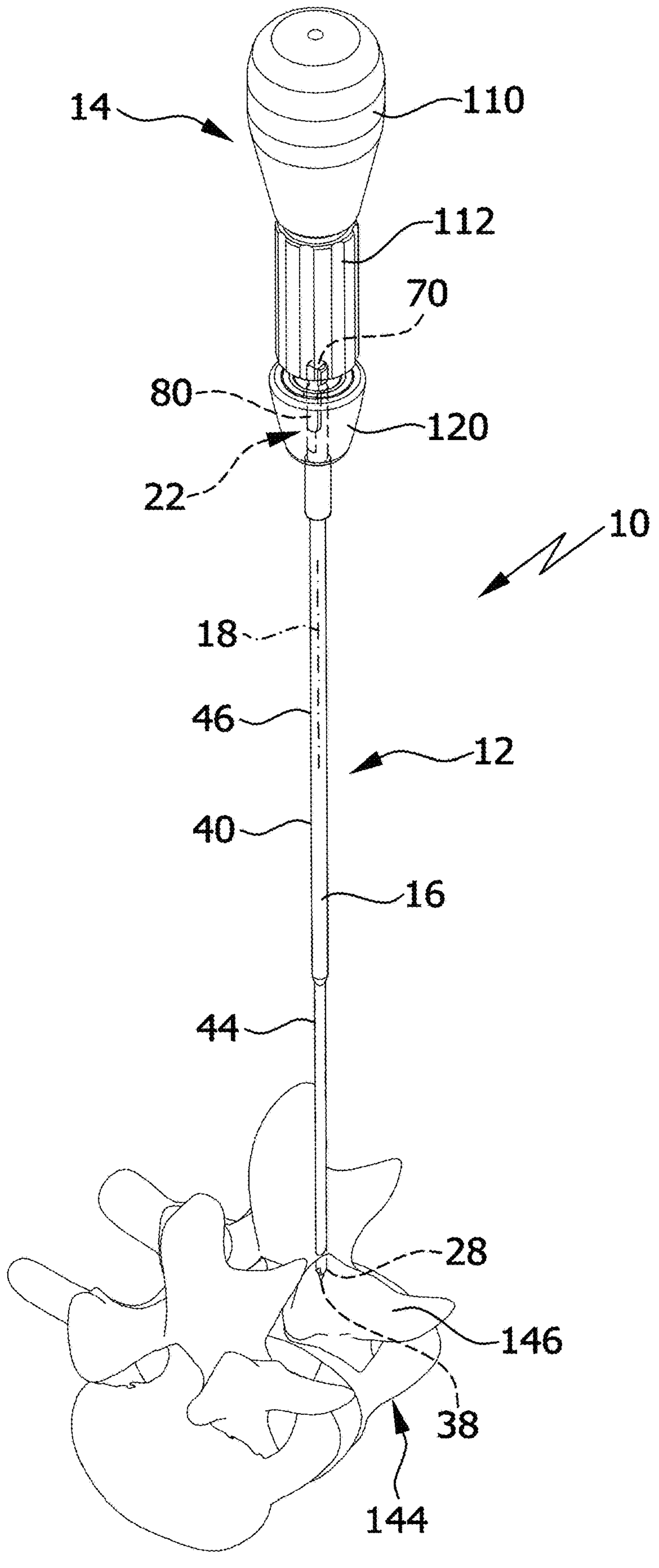
FIG. 1 shows a schematic perspective total view of a drilling system upon drilling open a vertebra.

Schematically depicted in FIG. 1 is an embodiment of a medical drilling system, denoted as a whole with the reference numeral 10. It comprises a drilling apparatus 12 and a handle 14 for coupling to the drilling apparatus 12, in particular in a rotationally fixed manner.

The drilling apparatus 12 comprises a cannulated drill 16 having a longitudinal channel 20 extending coaxially with a longitudinal axis 18 of the drill 16.

The drilling device 12 comprises at a proximal end a drilling apparatus coupling portion 22 for coupling to the handle 14 or a drilling machine in a rotationally-fixed manner, which are not depicted in the Figures.

The drill 16 has a proximal end 24 and a distal end 26. The distal end 26 is provided with a plurality of cutting edges 28, which are suitable, in particular, for cutting bone.

The drilling apparatus 12 also comprises a mandrin 30 with a distal mandrin portion 32 and a proximal mandrin portion 34. The distal mandrin portion 32 is of elongated rod-shaped configuration and defines a circular cross-section.

A tip 38 is formed at a distal end 36 of the distal mandrin portion 32.

The drill 16 has a drill shaft 40, which expands in outer diameter in one step in a transition region 42 commencing from the from the distal end 26 in the proximal direction. Thus, a distal shaft portion 44 and a proximal shaft portion 46 are defined, between which the transition region 42 is formed.

On the proximal side, the proximal shaft portion 46 is adjoined by a cylinder body 48. From a proximal end face 50 of the cylinder body 48, a cylindrical stop body 52 is configured projecting in the proximal direction. The stop body 52 has a slightly smaller outer diameter than the cylinder body 48, such that an annular face 54 pointing in the proximal direction is formed on the cylinder body. An end face 56 of the stop body 52 pointing in the proximal direction defines a stop face 58.

A drill coupling portion 60 projects in the proximal direction from the stop face 58. Thus, the drill 16 has the drill coupling portion 60 in the region of its proximal end 24. The drill coupling portion 60 together with the proximal mandrin portion 34 forms the drilling apparatus coupling portion 22.

Figure 2:
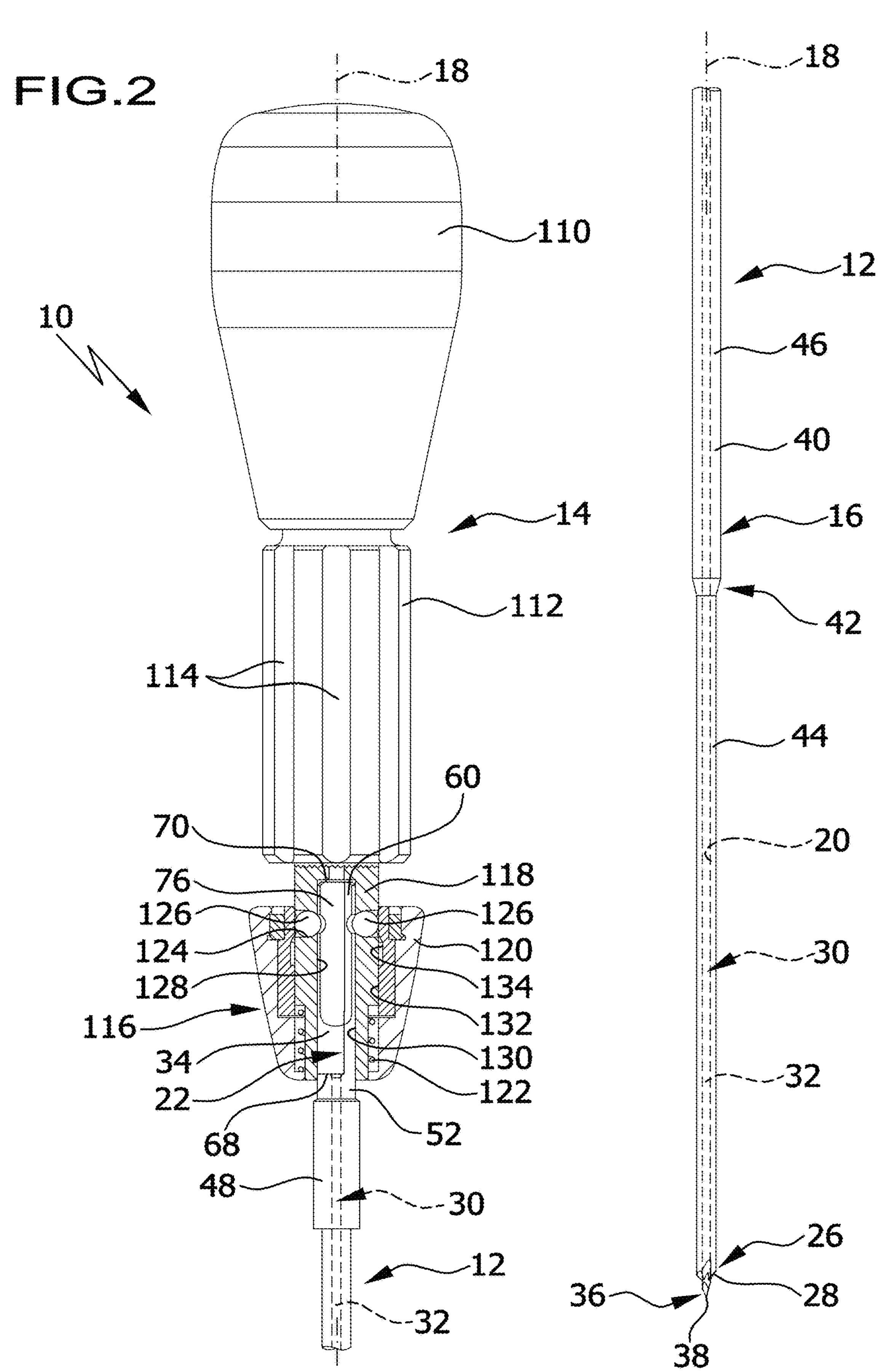
FIG. 2 shows a partially cut side view of the drilling system from FIG. 1.
Figures 3, 4:
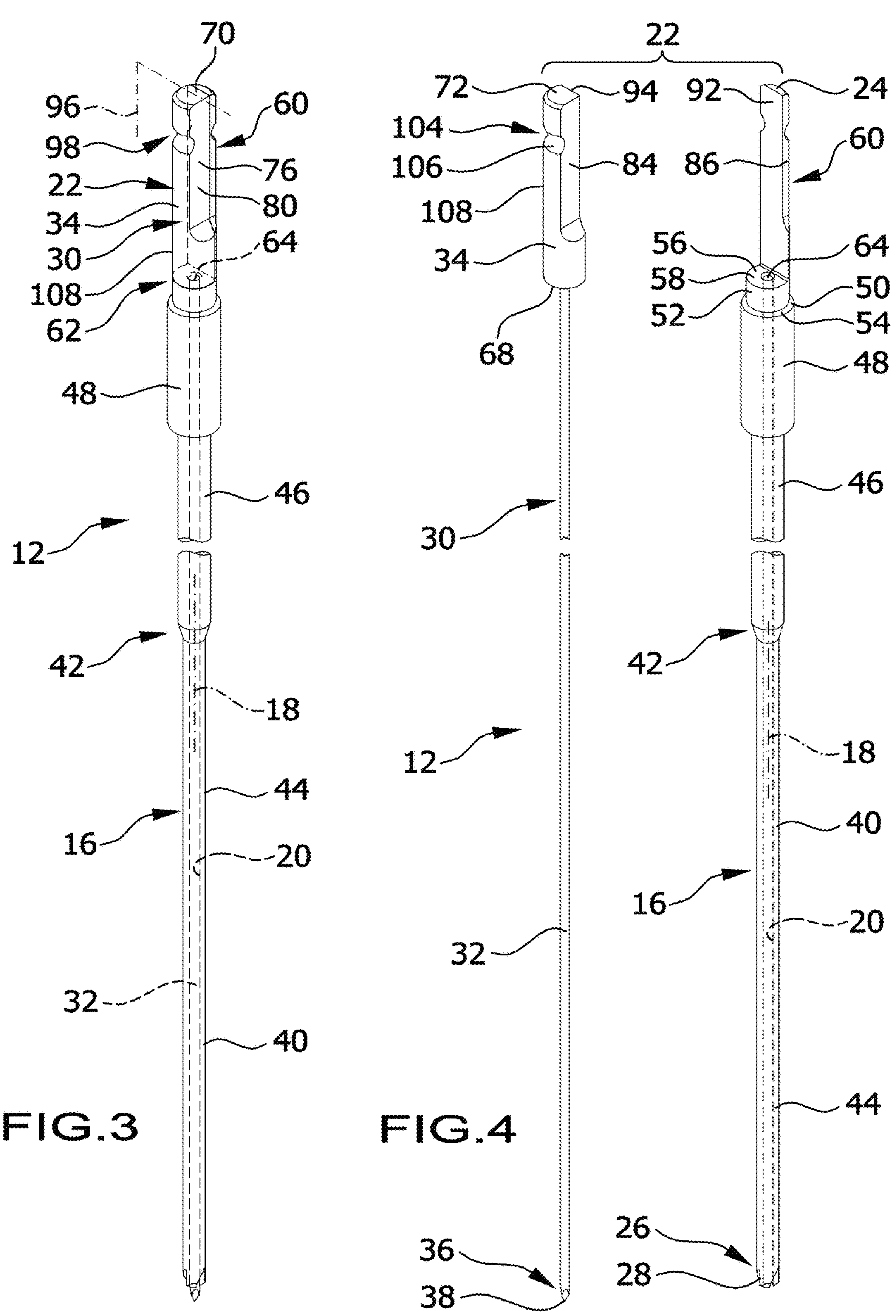
FIG. 3 shows a partially broken view of an embodiment of a drilling apparatus in the drilling position.
FIG. 4 shows a partially broken exploded view of the arrangement from FIG. 3.

The distal mandrin portion 32 is configured for insertion and closing the longitudinal channel 18 of the drill 16 over the entire length thereof in a drilling position, which is schematically depicted in FIGS. 1 to 3 as well as 5 and 6.

A cross-section of the distal mandrin portion 32 perpendicular to the longitudinal axis 18 corresponds to a cross-section of the longitudinal channel 20, such that the distal mandrin portion 32 fills the longitudinal channel 20 in a positive-locking manner. In the drilling position, the distal end 36 of the distal mandrin portion 32 reaches up to the distal end 26 of the longitudinal channel 20 or projects slightly beyond the distal end 26.

The longitudinal channel 20 has a circular cross-section. In alternative embodiments, the longitudinal channel 20 may also have an oval or otherwise non-round cross-section.

Figures 5, 6:
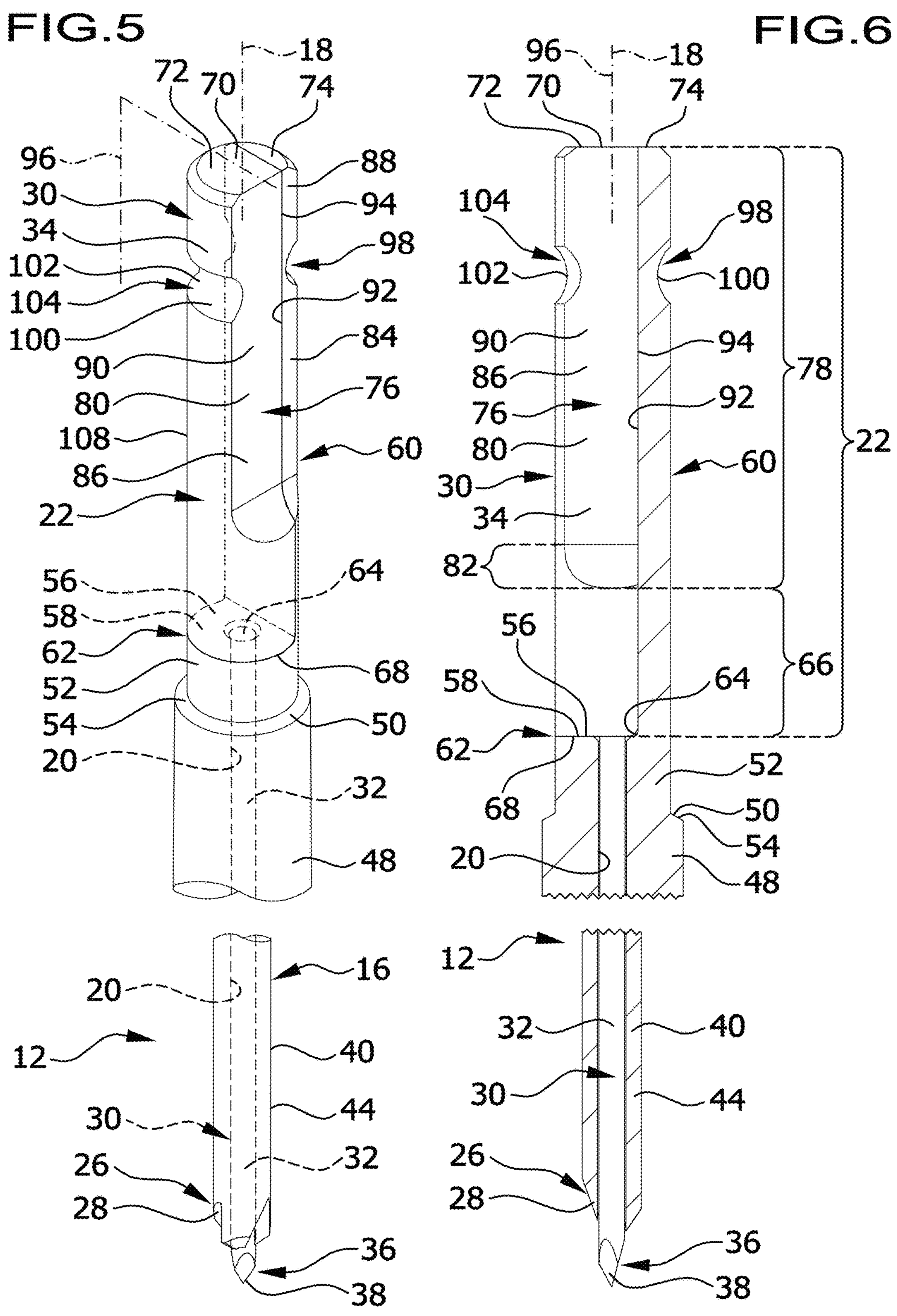
FIG. 5 shows enlarged views of proximal and distal ends of the drilling apparatus in the drilling position according to FIG. 3.
FIG. 6 shows a longitudinal section view of the arrangement from FIG. 5.

The stop body 52 forms with the stop face 58 a depth stop 62 for the mandrin 30 for delimiting an insertion depth of the distal mandrin portion 32 into the longitudinal channel 20. The proximal mandrin portion 34 in the drilling position abuts distally against the stop face 58 of the drill 16 pointing in the proximal direction, as can be easily seen in FIGS. 5 and 6.

The stop face 58 extends transversely, namely perpendicularly, to the longitudinal axis 18. It adjoins a proximal insertion opening 64 of the longitudinal channel 20. As can be easily seen in FIG. 5, the stop face 58 surrounds the insertion opening 64 at least partially, namely completely.

The proximal mandrin portion 34 is complemented by the drill coupling portion 60 in the region of the portion 66 to form a right circular cylinder, which extends the stop body 52 proximally in the drilling position.

The drilling apparatus coupling portion 22 extends from an end face 68 of the proximal mandrin portion 34 pointing in the distal direction up to a proximal end face 70 of the drilling apparatus coupling portion 22. The end face 70 extends transversely, namely perpendicularly, to the longitudinal axis 18.

The proximal end face 70 is formed in the drilling position by a proximal mandrin end face 72 of the proximal mandrin portion 34 and a proximal drill end face 74. The end face 68 is thus formed in part by the mandrin end face 72 and in part by the drill end face 74.

The drilling apparatus coupling portion 22 has a cylindrical basic shape, though which obtains a non-round cross-sectional area due to the formation of a flattened portion 76, namely in a coupling region 78 that proximally adjoins the portion 66 and reaches up to the end face 70. The flattened portion 76 is formed laterally and extends in parallel to the longitudinal axis 18. The flattened portion 76 thus defines a coupling face 80 on the drilling apparatus coupling portion 22, which thus also extends in parallel to the longitudinal axis 18.

The coupling face 80 is of planar configuration except for a short transition region 82 and comprises two coupling face portions 84, 86, namely a first coupling face portion 84, which is formed by a side face 88 of the drill coupling portion 60, and a second coupling face portion 86, which is formed by a side face 90 of the proximal mandrin portion 34.

Due to the formation of the flattened portion 76, the drilling apparatus coupling portion 22 is of rotationally asymmetrical configuration with respect to the longitudinal axis 18.

The drill coupling portion 60 is configured in such a way that it defines a drill entraining face 92. The proximal mandrin portion 34 defines a mandrin entraining face 94. In the drilling position, the drill entraining face 92 and the mandrin entraining face 94 abut against one another, as can be easily seen in FIGS. 5 and 6.

The drilling apparatus coupling portion 22 is of mirror-symmetrical configuration relative to a mirror plane 96 containing the longitudinal axis 18. The drill entraining face 92 and the mandrin entraining face 94 extend in parallel to the mirror plane 96.

As a result of the described configuration of the proximal mandrin portion 34 and the drill coupling portion 60, the mandrin 30 and the drill 16 are in engagement with one another in a rotationally fixed manner in the drilling position.

In this embodiment, both the drill coupling portion 60 and the proximal mandrin portion 34 are each individually of rotationally asymmetrical configuration with respect to the longitudinal axis 18.

Furthermore, a coupling element 98 is formed on the drilling apparatus coupling portion 22 for predetermining an axial position of the drilling apparatus 12 and the handle 14 relative to one another. The coupling element 98 is configured pointing in the radial direction relative to the longitudinal axis 18.

In one embodiment of the drilling apparatus 12 according to FIGS. 1 to 6, the coupling element 98 is configured in the form of a coupling receptacle 100. The coupling receptacle 100 partially surrounds the longitudinal axis 18. If no flattened portion 76 were provided in the drilling apparatus coupling portion 22, the coupling receptacle 100 would have the shape of an annular groove 102. In other words, this annular groove 102 and thus the coupling element 98 are interrupted by the flattened portion 76.

The coupling element 98 is formed partly on the proximal mandrin portion 34 and partly on the drill coupling portion 60.

A handling element 104 is also formed on the proximal mandrin portion 34. It has the form of a handling recess 106. The handling element 104 is configured pointing in the radial direction relative to the longitudinal axis 18.

In the embodiment of FIGS. 1 to 6, the handling element 104 is formed by the portion of the coupling element 98 that extends along an outer peripheral surface 108 of the proximal mandrin portion 34 with respect to the longitudinal axis 18.

The handle 14 depicted as an example comprises at its proximal end a knob 110 adjoined distally by a holding region 112 with grooves 114 extending in parallel to the longitudinal axis 18. The grooves 114 are arranged uniformly distributed over a circumference of the holding region 112.

A coupling device 116 forms a distal end region of the handle 14. Said coupling device is configured in the form of a quick coupling with a coupling sleeve 120 that is displaceable on a shaft 118 of the handle 14. The coupling device 116 enables the coupling of the handle 14 to the drilling apparatus 12 in a coupling position.

The coupling sleeve 120 is displaceable in the proximal direction against the action of a spring 122. When the pushed back coupling sleeve 120 is released, the spring 122 acts in such a way that the coupling sleeve 120 is automatically moved in the distal direction.

A plurality of balls 126 inserted in radial perforations 124 of the shaft 118 are held on said shaft 118. In the coupling position, in which the spring 122 holds the coupling sleeve 120 in its distal position, the balls 126 are pressed in the direction toward the longitudinal axis 18 and project somewhat beyond an inner wall face 128 of a coupling receptacle 130 formed in the shaft 118 coaxially with the longitudinal axis 18.

On the coupling sleeve 120, a recess 134 in the form of an annular groove pointing in the direction toward the longitudinal axis 18 is formed on an inner wall face 132, which points in the direction toward the longitudinal axis 18. Said annular groove has a depth such that the balls 126 can dip into the recess 134 so that they then release the coupling receptacle 130.

Furthermore, the coupling receptacle 130 has an inner, rotationally asymmetrical cross-section extending transversely to the longitudinal axis 18, which cross-section is adapted to the cross-section of the drilling apparatus coupling portion 22, so that the latter can be accommodated in the coupling receptacle 130 in a positive-locking manner. As a result of the described design, the drilling apparatus coupling portion 22 and the handle 14 are in engagement with one another in a rotationally fixed manner.

For coupling of the drilling apparatus 12 to the handle 14, the drilling apparatus coupling portion 22 is inserted with the proximal end face 70 in front into the distally open coupling receptacle 130 of the shaft 118 into the handle 14. The balls 126 thereby block the path of the drilling apparatus coupling portion 22. If the coupling sleeve 120 is now pushed in the direction of the holding region 112 against the action of the spring 122, the balls 126 can dip, as described, into the recess 134 and the drilling apparatus coupling portion 22 can be displaced further in the proximal direction, namely so far until the coupling receptacle 100 is located opposite the balls 126. When the coupling sleeve 120 is released, the spring 122 moves the coupling sleeve 120 relative to the holding region 112 in the distal direction, the balls 126 thereby being secured against a movement in the radial direction away from the longitudinal axis 18. FIG. 2 shows the described coupling position in which the handle 14 is coupled with its coupling device 116 to the drilling apparatus coupling portion 22 in a force-locking and/or positive-locking manner.

Alternatively, the coupling device 116 may also be configured in an analogous manner on a drilling machine, so that the drilling apparatus 12 can also be coupled accordingly to a drilling machine.

As described, the coupling device 116 can be brought from the coupling position into a release position in which it is out of engagement with the drilling apparatus coupling portion 22. The release position is not depicted in the Figures, but is described above. In the release position, the coupling sleeve 120 is thus displaced in the direction toward the holding region 112 against the action of the spring 122, so that the balls 126 dip into the recess 134 and release the drilling apparatus coupling portion 22.

Optionally, the coupling device 116 may comprise a pulling element for being brought into engagement with the at least one handling element 104, namely when the coupling device 116 adopts the release position. Thus, when the pulling element engages only into the handling element 104, which is formed on the proximal mandrin portion 34, the drilling apparatus 12 can be disassembled into its components with the aid of the handle 14. When the pulling element engages into the handling element 104, the mandrin 30 is pulled in the proximal direction out of the longitudinal channel 20 when the handle 14 is removed in the proximal direction.

A second embodiment of a drilling apparatus 12 is schematically depicted in FIGS. 7 to 10. The embodiment of the drilling apparatus 12 according to FIGS. 7 to 10 differs from the drilling apparatus 12 according to the embodiment of FIGS. 1 to 6 only in the configuration of the drilling apparatus coupling portion 22. For the description, the same reference numerals are thus used for identical or functionally similar components.

In this embodiment, the drill coupling portion 60 is configured mirror-symmetrically to the mirror plane 96 and thus comprises two mutually separate portions 136 and 138, which are separated from one another, namely spaced at a distance from one another, by a coupling slot 140 extending in parallel to the longitudinal axis 18. The coupling slot 140 has two mutually facing slot faces 142, which form the drill entraining faces 92.

Figures 7, 8:
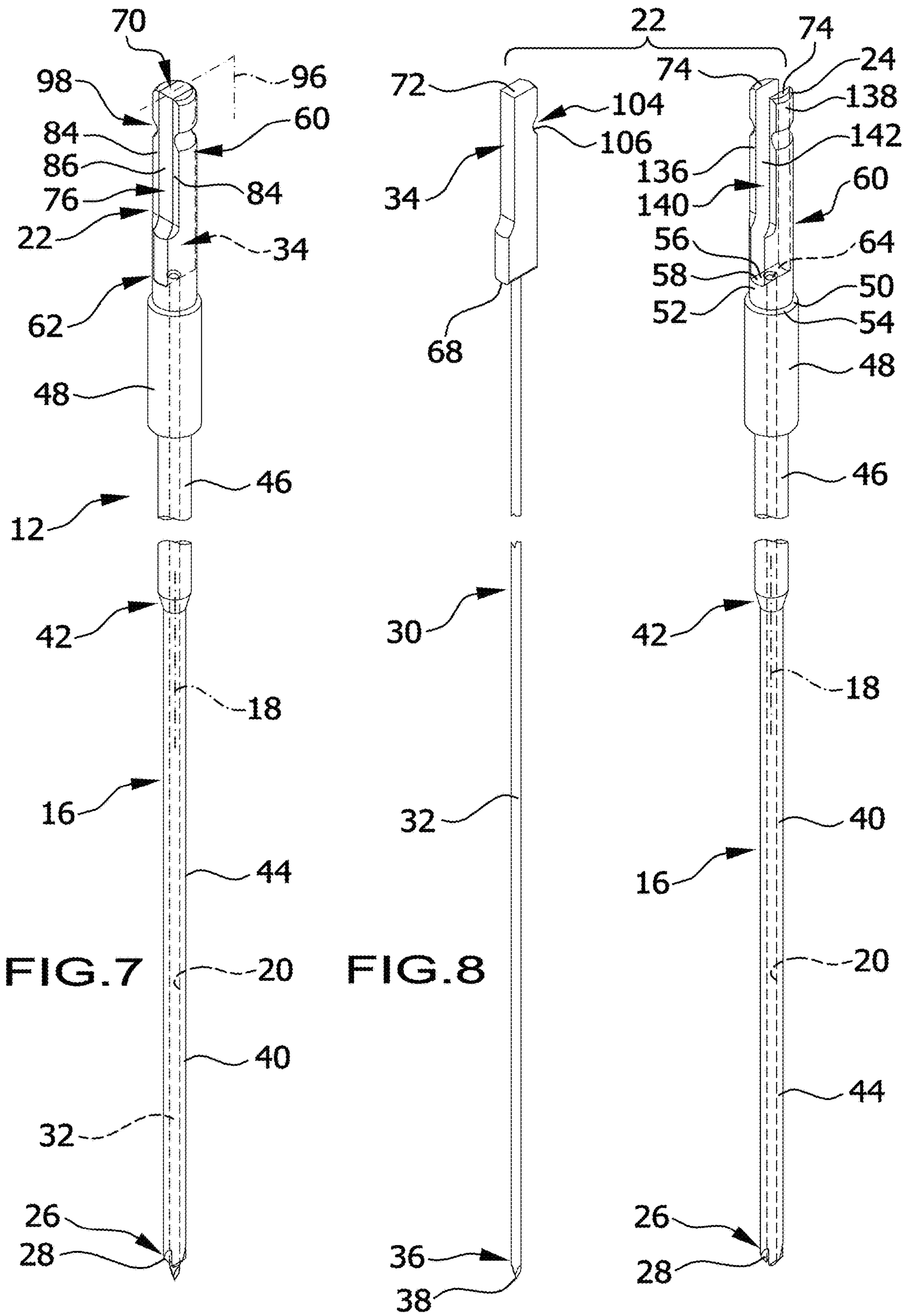
FIG. 7 shows a view analogous to FIG. 3 of a further embodiment of a drilling apparatus.
FIG. 8 shows a view analogous to FIG. 4 of the drilling apparatus from FIG. 7.
Figures 9, 10:
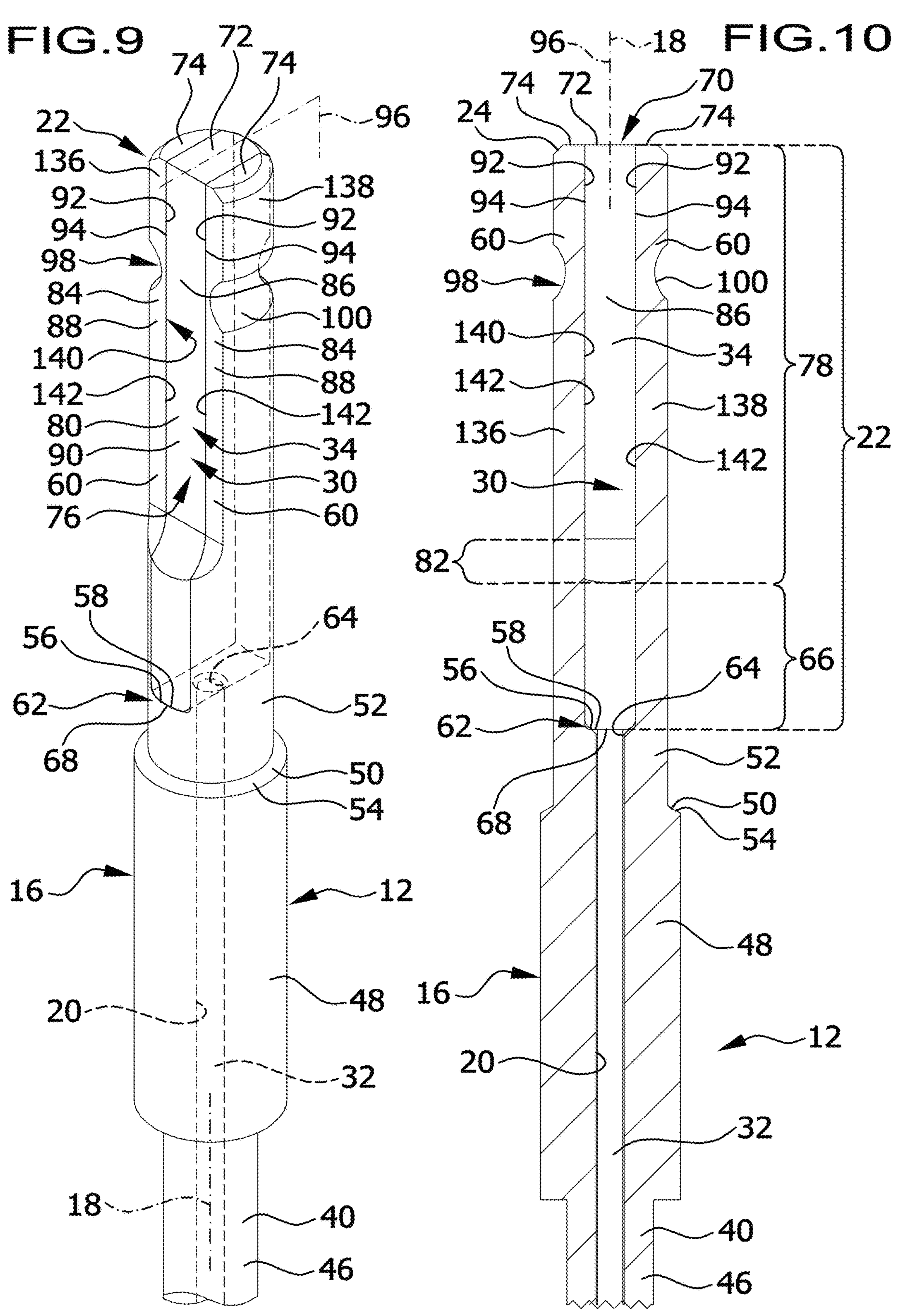
FIG. 9 shows an enlarged view of a proximal end of the drilling apparatus from FIG. 7.
FIG. 10 shows a longitudinal section view of the arrangement from FIG. 9.

In this embodiment, the proximal mandrin portion 34 is configured mirror-symmetrically to itself relative to the mirror plane 96 and in the drilling position engages into the coupling slot 140 such that it fills it. The drilling position in this embodiment is schematically depicted in FIGS. 7, 9 and 10.

An outer contour of the drilling apparatus coupling portion 22 is identical to an outer contour of the drilling apparatus coupling portion 22 of the embodiment of FIGS. 1 to 6.

Due to the slotted configuration of the drill coupling portion 60, it has two drill entraining faces 92 extending in parallel to the longitudinal axis 18 and in parallel to one another and facing toward one another. The proximal mandrin portion 34 accordingly has two mandrin entraining faces 94. These face away from one another in opposite directions and also extend in parallel to one another and in parallel to the longitudinal axis 18. As can be easily seen in FIG. 10, the drill entraining faces 92 and the mandrin entraining faces 94 abut against one another in the drilling position.

The stop face 58 extends between the mutually facing drill entraining faces 92 and is formed by the end face 56 of the stop body 52.

In this embodiment, too, the handling element 104 is configured in the form of a handling recess 106, namely as part of the coupling element 98.

In the embodiment of FIGS. 7 to 10, the coupling face 80 is formed by two first coupling face portions 84 on the portions 136 and 138 of the drill coupling portion 60 and by a second coupling portion 86 on the proximal mandrin portion 34.

Accordingly, the proximal end face 70 is also formed by three parts, namely a proximal mandrin end face 72, which in the drilling position is arranged between two proximal drill end faces 74.

The functioning of the drilling apparatus 12 according to the embodiment of FIGS. 7 to 10 corresponds in its entirety to the functioning of the embodiment of the drilling apparatus 12 according to FIGS. 1 to 6, such that reference can be made to the preceding description.

In the embodiments described, the drill 16 is made of a metallic material. The mandrin 30 is also made of a metallic material.

In alternative embodiments, the mandrin 30 is made of a plastic material.

In all embodiments, the drilling apparatus 12 is made of at least one sterilizable material. It may be made of one single sterilizable material, for example a sterilizable metallic material. If, for example, the mandrin 30 is made of a plastic material and the drill 16 is made of a metallic material, the drilling apparatus 12 is made of two sterilizable materials.

Figure 11:
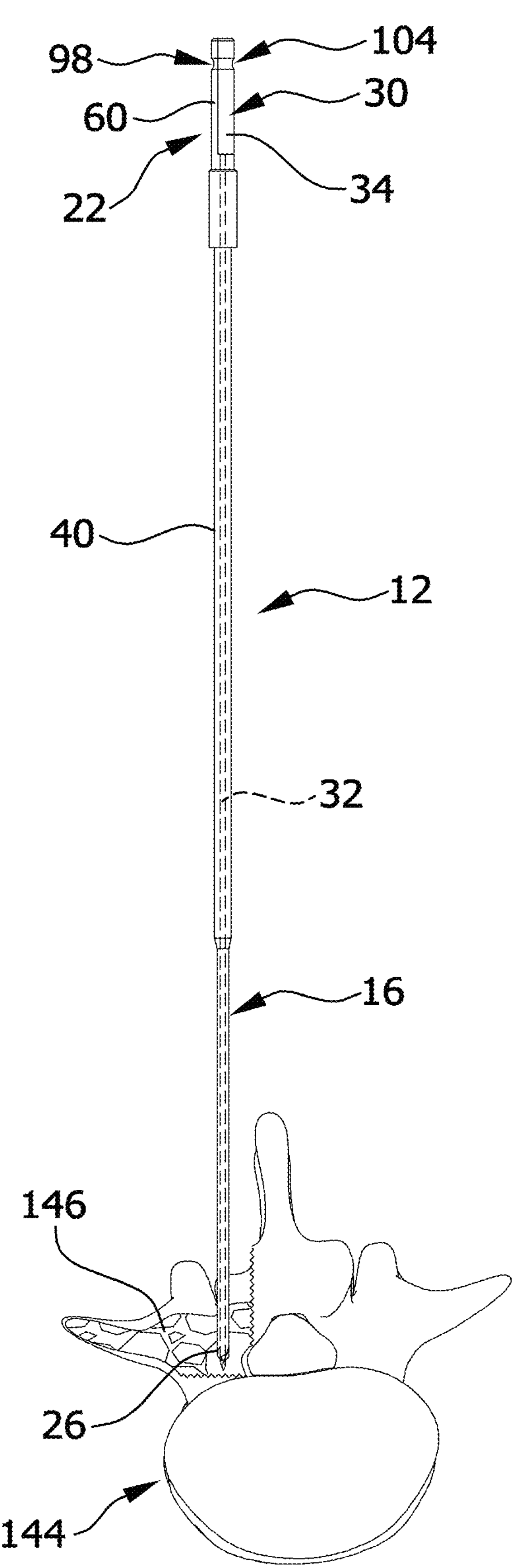
FIG. 11 shows a schematic view upon positioning a drilling apparatus on a bone.
Figure 14:
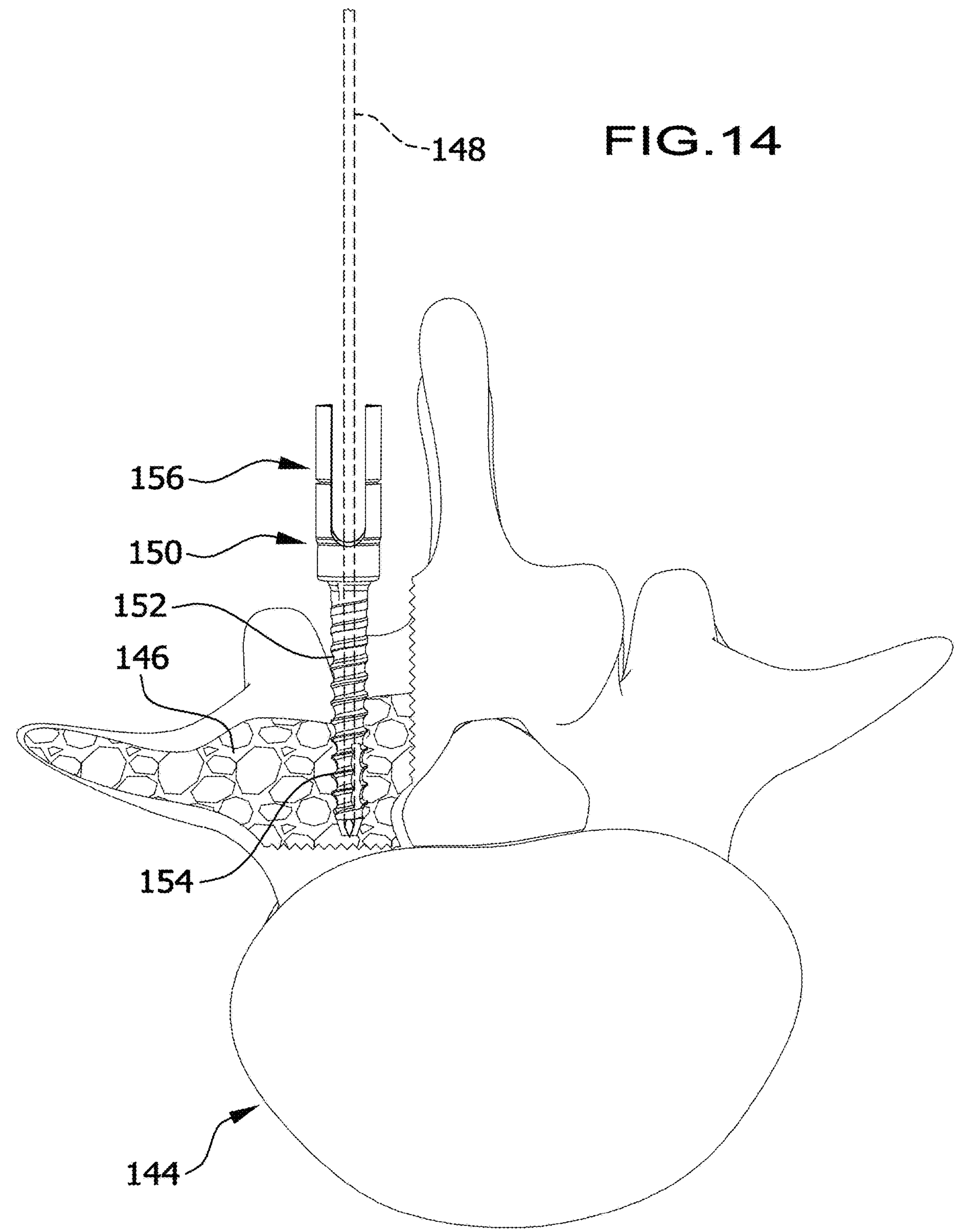
FIG. 14 shows a schematic view similar to FIG. 12 after removal of the drill over the K-wire and introduction of a pedicle screw over the K-wire into the pedicle.

The use of the drilling system 10 is briefly described in the following schematically in connection with FIGS. 11 and 14 based on a possible application. In spinal surgery, for example, there are not only pedicle screws. For the cervical spine, for example, there are also lateral mass screws. The procedure described in the following is not a limitation of the area of use of the drilling apparatus 12 for use in connection with pedicle screws 150.

Figure 12:
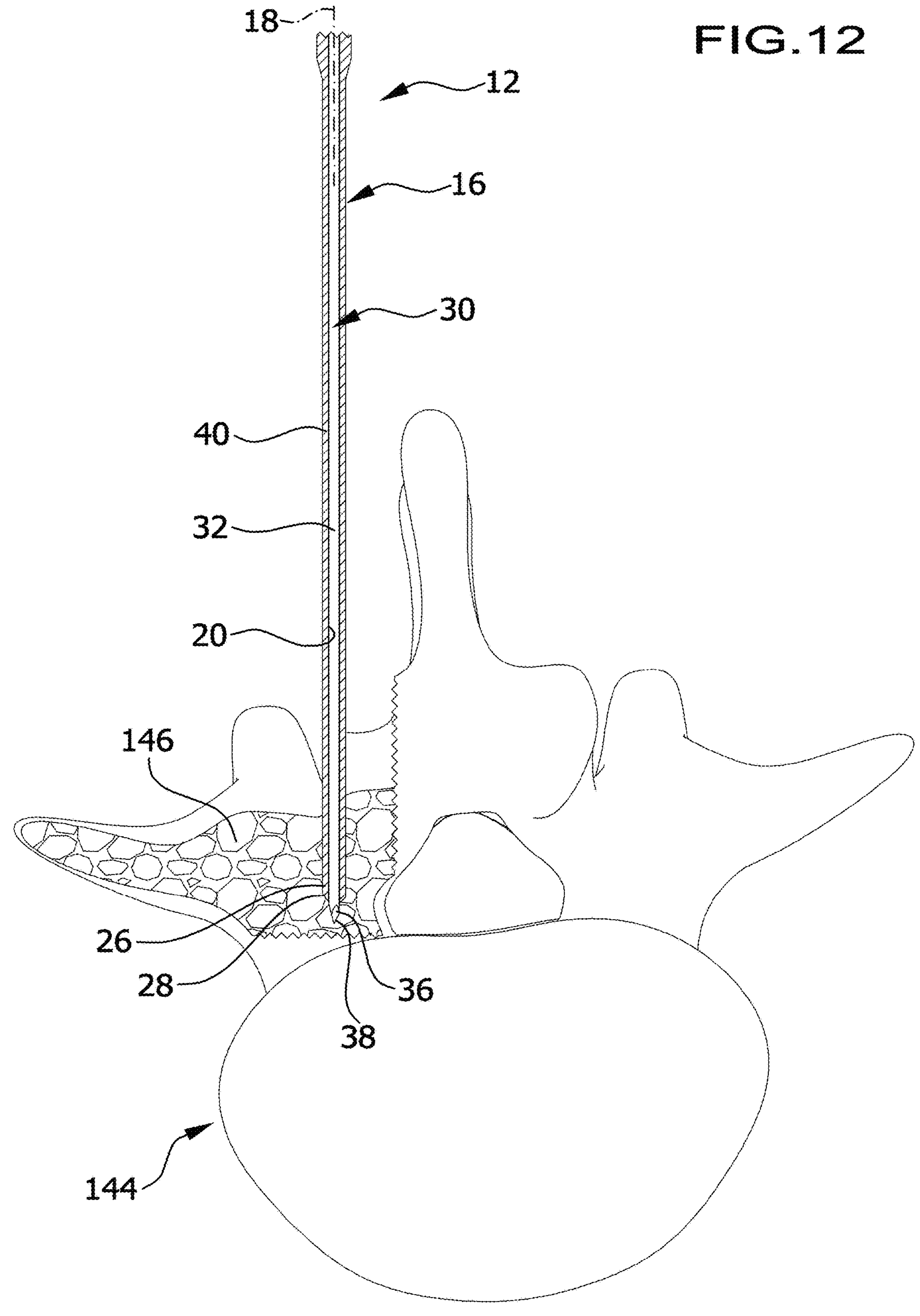
FIG. 12 shows a schematic, partially broken view of a drilling apparatus driven into a pedicle.

In a first step, the drilling apparatus 12 is inserted with its distal end 26 through a minimally invasive access point into the body of a patient. FIGS. 11 and 12 show this procedure schematically, neither the handle 14 nor a correspondingly suited drilling machine being depicted for clarity reasons.

The drill 16 with the mandrin 30 is anchored in a pedicle 146 of the vertebra 144. When drilling, the mandrin 30 prevents bone substance from being able to enter into the longitudinal channel 20 and clog it.

In a next step, the mandrin 30 is pulled out of the longitudinal channel 20 of the drill 16. However, the drill 16 remains in the vertebra 144.

After the mandrin 30 has unblocked the longitudinal channel 20, a K-wire 148 comprised by the drilling system 10 can be inserted coming from the proximal side through the insertion opening 64 into the longitudinal channel 20 and be anchored in the vertebra 144. The drill 16 hereby serves as a guide for the K-wire 148.

Figure 13:
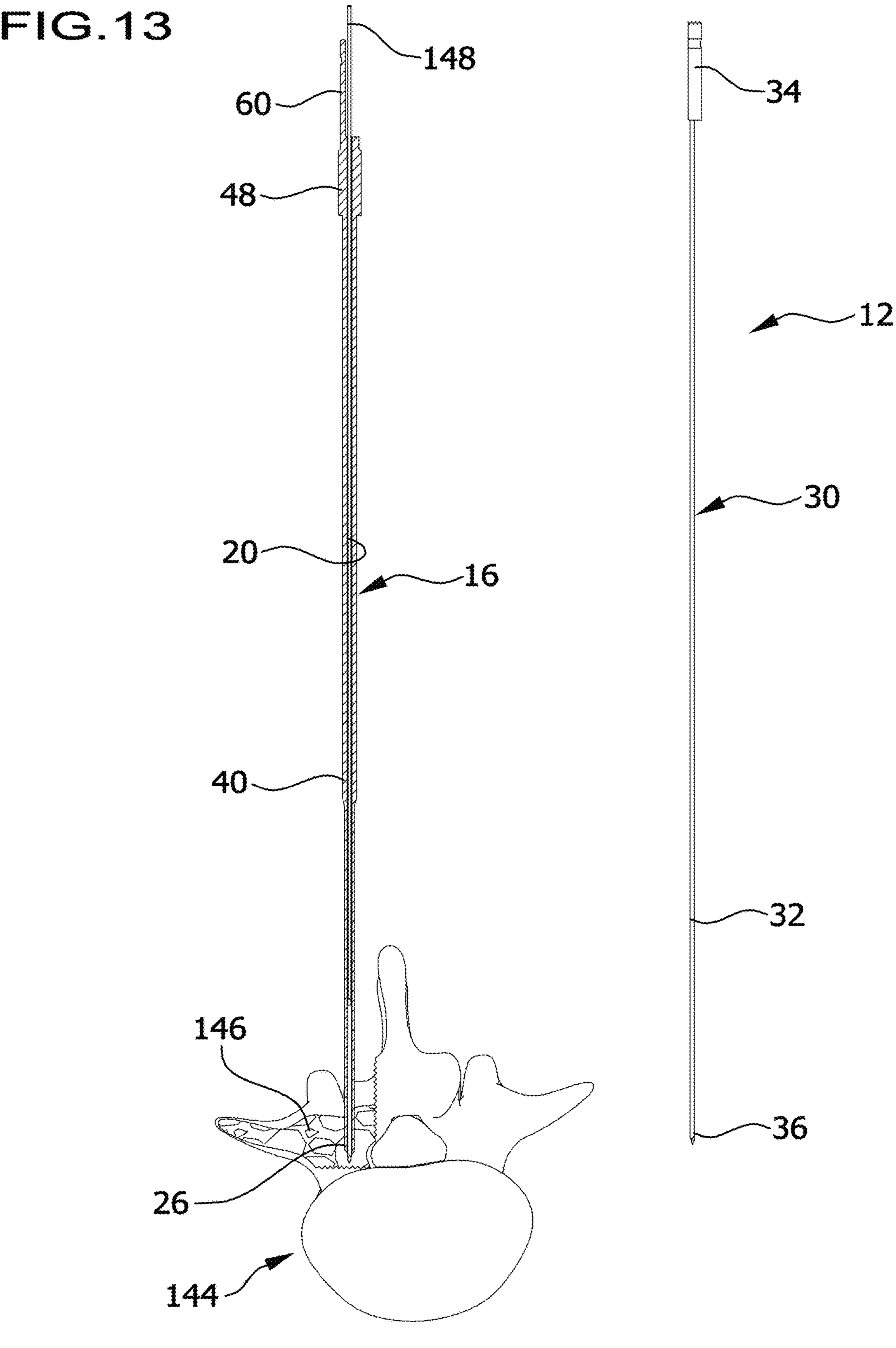
FIG. 13 shows a schematic view similar to FIG. 11 with a drill still in the pedicle after removal of the mandrin and insertion of a K-wire through the longitudinal channel of the drill into the pedicle.

When the K-wire 148 is anchored, as is schematically depicted in FIG. 13, in a next step, the drill 16 can be removed from the vertebra 144, the K-wire 148 remaining in the vertebra 144.

The K-wire 148 now serves to guide a cannulated pedicle screw 150. The latter can then be screwed into the pedicle 146 in the typical manner with a shaft 154 provided with an external thread 152.

When the pedicle screw 150 is sufficiently anchored in the vertebra 144, the K-wire 148 is removed. The pedicle screw 150 can now optionally be driven further into the vertebra 144.

A head 156 of the pedicle screw 150 is configured to accommodate a rod-shaped connecting element not shown in the Figures, which can be secured in the head 156 in a clamping manner with a fixing screw not shown in the Figures.

After placing a first pedicle screw 150 in the described manner, the mandrin 30 can be brought with its distal mandrin portion 32 from a separating position, in which the mandrin 30 and the drill 16 are completely out of engagement, back into the drilling position by inserting the distal mandrin portion 32 into the longitudinal channel 20 commencing from its proximal end. Thus, it is possible to anchor a plurality of pedicle screws 150 in vertebrae 144 in the above-described manner with only one single drilling apparatus 12 during a surgical procedure.

REFERENCE NUMERAL LIST

10 drilling system
12 drilling apparatus
14 handle
16 drill
18 longitudinal axis
20 longitudinal channel
22 drilling apparatus coupling portion
24 proximal end
26 distal end
28 cutting edge
30 mandrin
32 distal mandrin portion
34 proximal mandrin portion
36 distal end
38 tip
40 drill shaft
42 transition region
44 distal shaft portion
45 proximal shaft portion
48 cylinder body
50 end face
52 stop body
54 annular face
56 end face
58 stop face
60 drill coupling portion
62 depth stop
64 insertion opening
66 portion
68 end face
70 proximal end face
72 proximal mandrin end face
74 proximal drill end face
76 flattened portion
78 coupling region
80 coupling face
82 transition region
84 first coupling face portion
86 second coupling face portion
88 side face
90 side face
92 drill entraining face
94 mandrin entraining face
96 mirror plane
98 coupling element
100 coupling receptacle
102 annular groove
104 handling element
106 handling recess
108 peripheral surface
110 knob
112 holding region
114 groove
116 coupling device
118 shaft
120 coupling sleeve
122 spring
124 perforation
126 ball
128 wall face
130 coupling receptacle
132 wall face
134 recess
136 portion
138 portion
140 coupling slot
142 slot face
144 vertebra
146 pedicle
148 K-wire
150 pedicle screw
152 external thread
154 shaft
156 head

The invention claimed is:

1. A medical drilling apparatus comprising:

wherein each at least one mandrin entraining face comprises a planar surface a drill that is cannulated, the drill comprising a longitudinal channel extending coaxially with a longitudinal axis of the drill;

a drilling apparatus coupling portion at a proximal end of the medical drilling apparatus, the drilling apparatus coupling portion configured for coupling to a handle or a drilling machine in a rotationally fixed manner; and a mandrin comprising a proximal mandrin portion and a distal mandrin portion, the distal mandrin portion configured for inserting into and closing the longitudinal channel of the drill over a length of the drill in a drilling position, the drill further comprising a drill proximal end, a drill distal end, and a drill coupling portion in a region of the drill proximal end, and the drill coupling portion and the proximal mandrin portion forming the drilling apparatus coupling portion, wherein the drill coupling portion has at least one drill entraining face extending parallel to the longitudinal axis, wherein the proximal mandrin portion has at least one mandrin entraining face extending parallel to the longitudinal axis, and wherein the at least one drill entraining face and the at least one mandrin entraining face abut against one another in face-to-face contact in the drilling position to thereby prevent relative rotation between the drill and the mandrin about the longitudinal axis, wherein each at least one mandrin entraining face comprises a planar surface.

2. The medical drilling apparatus according to claim 1, wherein the drilling apparatus coupling portion is of rotationally asymmetrical configuration with respect to the longitudinal axis.

3. The medical drilling apparatus according to claim 1, wherein the drill coupling portion comprises a coupling slot extending in parallel to the longitudinal axis, and wherein the proximal mandrin portion engages into the coupling slot in the drilling position.

4. The medical drilling apparatus according to claim 3, wherein, the coupling slot has two mutually facing slot faces that form the at least one drill entraining face, and the mandrin has two mutually opposed outer faces that form the at least one mandrin entraining face.

5. The medical drilling apparatus according to claim 1, wherein the drilling apparatus coupling portion has a coupling face that extends in parallel to the longitudinal axis and transversely to the at least one drill entraining face.

6. The medical drilling apparatus according to claim 5, wherein the coupling face is of planar or substantially planar configuration and comprises at least two coupling face portions, wherein at least one of the at least two coupling face portions is formed by a side face of the drill coupling portion, and wherein at least one further one of the at least two coupling face portions is formed by a side face of the proximal mandrin portion.

7. The medical drilling apparatus according to claim 1, wherein the at least one mandrin entraining face and the at least one drill entraining face extend in parallel to a mirror plane containing and parallel to the longitudinal axis.

8. The medical drilling apparatus according to claim 1, wherein the distal mandrin portion has a cross-section that corresponds to a cross-section of the longitudinal channel.

9. The medical drilling apparatus according to claim 1, wherein the drilling apparatus coupling portion is of mirror-symmetrical configuration relative to a mirror plane containing and parallel to the longitudinal axis.

10. The medical drilling apparatus according to claim 9, wherein the drill coupling portion and the proximal mandrin portion are each of mirror-symmetrical configuration relative to the mirror plane.

11. The medical drilling apparatus according to claim 1, wherein a depth stop for the mandrin is arranged or formed on the drill for delimiting an insertion depth of the distal mandrin portion into the longitudinal channel.

12. The medical drilling apparatus according to claim 11, wherein the depth stop comprises a stop face of the drill pointing in a proximal direction, the proximal mandrin portion comprises a distal side, and the distal side of the proximal mandrin portion abuts against the stop face of the drill in the drilling position.

13. The medical drilling apparatus according to claim 1, wherein the drilling apparatus coupling portion has a rotationally symmetrical basic shape and a lateral flattened portion extending in parallel to the longitudinal axis.

14. The medical drilling apparatus according to claim 1, wherein the drill coupling portion and the proximal mandrin portion are each individually of rotationally asymmetrical configuration with respect to the longitudinal axis.

15. The medical drilling apparatus according to claim 1, wherein at least one coupling element is arranged or formed on the drilling apparatus coupling portion for predetermining an axial position of the medical drilling apparatus and a handle or a drilling machine relative to one another.

16. The medical drilling apparatus according to claim 15, wherein the at least one coupling element:

points in a radial direction;

comprises a coupling projection or a coupling receptacle;

at least partially surrounds the longitudinal axis; and/or is interrupted by a flattened portion, wherein the drilling apparatus coupling portion has a rotationally symmetrical basic shape and the flattened portion extends in parallel to the longitudinal axis.

17. The medical drilling apparatus according to claim 1, wherein at least one handling element is arranged or formed on the proximal mandrin portion.

18. The medical drilling apparatus according to claim 1, wherein the drill coupling portion has two drill entraining faces, and wherein the proximal mandrin portion has two mandrin entraining faces.

19. A medical drilling system comprising:

the medical drilling apparatus according to claim 1; and a handle and/or a drilling machine for coupling to the medical drilling apparatus in a rotationally fixed manner.

20. The medical drilling system according to claim 19, wherein:

a) the medical drilling system comprises at least one K-wire; and/or b) the handle and/or the drilling machine comprise a coupling device for coupling to the drilling apparatus coupling portion in a force-locking and/or positive-locking manner in a coupling position.

* * * * *